(12) United States Patent
Arndt et al.

(10) Patent No.: US 10,918,751 B2
(45) Date of Patent: Feb. 16, 2021

(54) SYSTEMS AND METHOD FOR DECONTAMINATING A TUBE

(71) Applicants: Dickey Arndt, Friendswood, TX (US); Diane Byerly, Seabrook, TX (US); Timothy Kennedy, Sugar Land, TX (US); Gregory Lin, Friendswood, TX (US); Patrick W. Fink, Missouri City, TX (US); Billy G. Smith, Houston, TX (US)

(72) Inventors: Dickey Arndt, Friendswood, TX (US); Diane Byerly, Seabrook, TX (US); Timothy Kennedy, Sugar Land, TX (US); Gregory Lin, Friendswood, TX (US); Patrick W. Fink, Missouri City, TX (US); Billy G. Smith, Houston, TX (US)

( * ) Notice: Subject to any disclaimer, the term of this patent is extended or adjusted under 35 U.S.C. 154(b) by 0 days.

(21) Appl. No.: 17/016,755

(22) Filed: Sep. 10, 2020

(65) Prior Publication Data

US 2020/0405896 A1 Dec. 31, 2020

Related U.S. Application Data

(62) Division of application No. 16/002,005, filed on Jun. 7, 2018.

(51) Int. Cl.
| | |
|---|---|
| *A61L 2/12* | (2006.01) |
| *A61M 39/08* | (2006.01) |
| *H05B 6/68* | (2006.01) |
| *H05B 6/72* | (2006.01) |
| *A61M 25/00* | (2006.01) |

(52) U.S. Cl.
CPC ............... *A61L 2/12* (2013.01); *A61M 39/08* (2013.01); *H05B 6/686* (2013.01); *H05B 6/72* (2013.01); *A61M 2025/0019* (2013.01); *A61M 2209/10* (2013.01)

(58) Field of Classification Search
CPC . A61L 2/12; H05B 6/686; H05B 6/72; A61M 39/08; A61M 2025/0019; A61M 2209/10
See application file for complete search history.

(56) References Cited

U.S. PATENT DOCUMENTS

| | | |
|---|---|---|
| 3,691,338 A | 9/1972 | Chang |
| 4,620,593 A | 11/1986 | Haagensen |
| 5,823,197 A | 10/1998 | Edwards |
| 5,827,277 A | 10/1998 | Edwards |
| 5,843,077 A | 12/1998 | Edwards |
| 6,016,452 A | 1/2000 | Kasevich |
| 7,950,397 B2 | 5/2011 | Thapliyal |

(Continued)

*Primary Examiner* — Regina M Yoo
(74) *Attorney, Agent, or Firm* — MH2 Technology Law Group LLP

(57) ABSTRACT

A method for decontaminating a tube includes positioning an antenna at least partially within the tube. The tube is positioned at least partially within a living body. The method also includes decontaminating the tube by causing the antenna to emit electromagnetic waves having a frequency from about 10 GHz to about 100 GHz for a time duration that is less than or equal to 60 seconds. The electromagnetic waves cause a temperature of the living body proximate to the tube to increase from about 0.1° C. to about 3° C. so as to not substantially damage the living body.

20 Claims, 14 Drawing Sheets

(56) References Cited

U.S. PATENT DOCUMENTS

| | | |
|---|---|---|
| 8,146,603 B2 | 4/2012 | Thapliyal |
| 8,287,527 B2 | 10/2012 | Brannan |
| 8,346,370 B2 | 1/2013 | Haley |
| 8,545,493 B2 | 10/2013 | Brannan |
| 8,647,585 B2 | 2/2014 | Hancock |
| 8,797,039 B2 | 8/2014 | Brannan |
| 8,880,195 B2 | 11/2014 | Azure |
| 8,900,521 B2 | 12/2014 | Hancock |
| 8,934,989 B2 | 1/2015 | Ormsby |
| 9,024,237 B2 | 5/2015 | Bonn |
| 9,042,958 B2 | 5/2015 | Karmarkar |
| 9,060,750 B2 | 6/2015 | Lam |
| 9,427,285 B2 | 8/2016 | Deem |
| 10,194,971 B2 | 2/2019 | Wegrzyn, III |
| 10,492,860 B2 | 12/2019 | Hagness |
| 2001/0003798 A1 | 6/2001 | McGovern |
| 2005/0249667 A1 | 11/2005 | Tuszynski |
| 2008/0097193 A1* | 4/2008 | Karmarkar ............... A61B 5/06 600/423 |
| 2009/0076494 A1 | 3/2009 | Azure |
| 2009/0118610 A1 | 5/2009 | Karmarkar |
| 2009/0236333 A1 | 9/2009 | Ben-Shmuel |
| 2009/0248006 A1 | 10/2009 | Paulus |
| 2010/0082025 A1 | 4/2010 | Brannan |
| 2010/0268218 A1 | 10/2010 | Ormsby |
| 2014/0378958 A1 | 12/2014 | Leussler |
| 2015/0123688 A1 | 5/2015 | Sappok |
| 2015/0374471 A1 | 12/2015 | Stangel |

\* cited by examiner

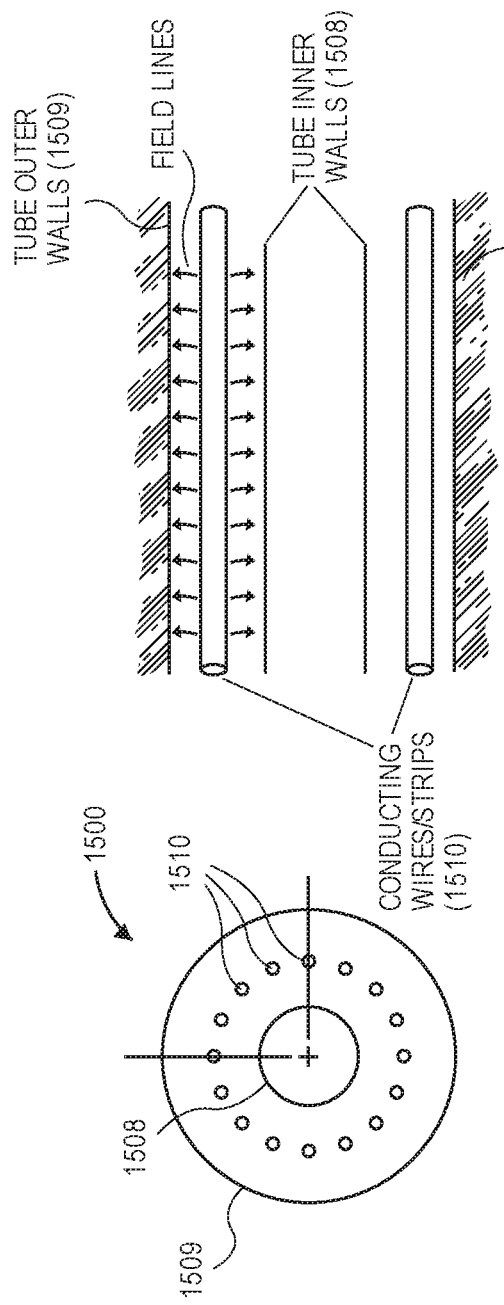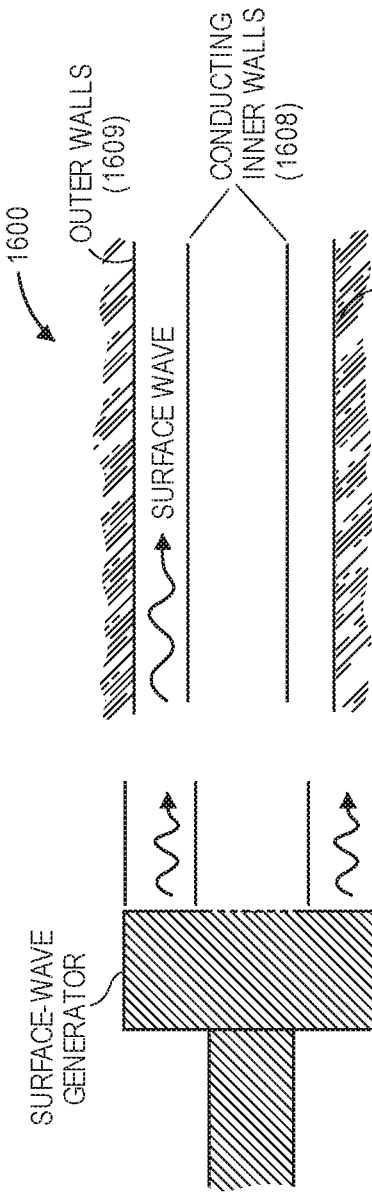

SYSTEMS AND METHOD FOR DECONTAMINATING A TUBE

CROSS-REFERENCE TO RELATED APPLICATIONS

This application is a divisional of U.S. patent application Ser. No. 16/002,005, filed on Jun. 7, 2018, which is incorporated herein by reference.

BACKGROUND

Microbial biofilms form when bacteria adheres to surfaces in aqueous environments. For example, microbial biofilms may form in fluid systems aboard spacecrafts and in space suits (e.g., cooling loops, low nutrient urine and waste lines), increasing the potential for fouling and corrosion during spaceflight. Microbial biofilms are also a problem in the medical community, particularly in ports and catheters that are inserted into patients. When such biofilms are present (e.g., at the interface between the exterior wall of the tubing and the surrounding human tissue), the port/catheter is oftentimes replaced, which is time-consuming, costly, painful, and potentially dangerous to the patient. Microbial biofilms are also present in the oil and gas industry. For example, such biofilms may be present within tubing strings in a wellbore or in transportation pipelines. Conventional methodologies for eradicating biofilms vary depending on the application and are often invasive, especially when dealing with medical patients.

SUMMARY

A method for decontaminating a tube is disclosed. The method includes positioning an antenna at least partially within the tube. The tube is positioned at least partially within a living body. The method also includes decontaminating the tube by causing the antenna to emit electromagnetic waves having a frequency from about 10 GHz to about 100 GHz for a time duration that is less than or equal to 60 seconds. The electromagnetic waves cause a temperature of the living body proximate to the tube to increase from about 0.1° C. to about 3° C. so as to not substantially damage the living body.

In another embodiment, the method includes positioning an antenna at least partially within the tube. The tube is positioned at least partially within a living body. The method also includes decontaminating the tube without substantially damaging the living body by causing the antenna to emit electromagnetic waves having a power from about 0.1 W to about 5 W and a frequency from about 10 GHz to about 100 GHz for a time duration that is less than or equal to 40 seconds. The electromagnetic waves cause a temperature of the living body proximate to the tube to increase by less than about 2.5° C. The method also includes measuring the temperature of the living body proximate to the tube with a sensor while the electromagnetic waves are emitted. The method also includes transmitting the temperature of the living body proximate to the tube to a controller. The method also includes modifying the power, the frequency, the time duration, or a combination thereof of the electromagnetic waves with the controller when the temperature of the living body proximate to the tube is greater than a predetermined threshold, thereby causing the temperature of the living body proximate to the tube to decrease.

In another embodiment, the method includes positioning an antenna and a buffer at least partially within the tube. The tube is positioned at least partially within a living body. The method also includes moving the antenna and the buffer axially within the tube. The buffer contacts an inner surface of the tube and prevents the antenna from contacting the inner surface of the tube. The method also includes decontaminating the tube without substantially damaging, fusing, or ablating any portion of the living body by causing the antenna to emit electromagnetic waves while the antenna moves axially within the tube. The electromagnetic waves have a power from about 0.1 W to about 5 W and a frequency from about 10 GHz to about 100 GHz. The electromagnetic waves are emitted for a time duration that is less than or equal to 40 seconds. Greater than about 75% of an energy from the electromagnetic waves is absorbed by the living body within 1 mm from the tube. The electromagnetic waves cause a temperature of the living body proximate to the tube to increase by less than about 2.5° C. while the temperature of the living body does not exceed 40° C. The method also includes measuring the temperature of the living body proximate to the tube with a sensor that is coupled to an outer surface of the tube. The method also includes transmitting the temperature of the living body proximate to the tube to a controller. The method also includes modifying the power, the frequency, the time duration, or a combination thereof of the electromagnetic waves with the controller when the temperature of the living body proximate to the tube is greater than a predetermined threshold, thereby causing the temperature of the living body proximate to the tube to decrease.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The accompanying drawings, which are incorporated in and constitute a part of this specification, illustrate embodiments of the present teachings and together with the description, serve to explain the principles of the present teachings. In the figures:

FIGS. 15(A) and 15(B) illustrate schematic side cross-sectional views of another tube (e.g., a port) with conducting wires/strips embedded within the walls of the catheter, according to an embodiment.

FIG. 16 illustrates a schematic side cross-sectional view of another tube (e.g., a port) with a microwave surface wave generated and propagating down through the catheter walls and radiating energy as it propagates, according to an embodiment.

DETAILED DESCRIPTION

Figure 1:
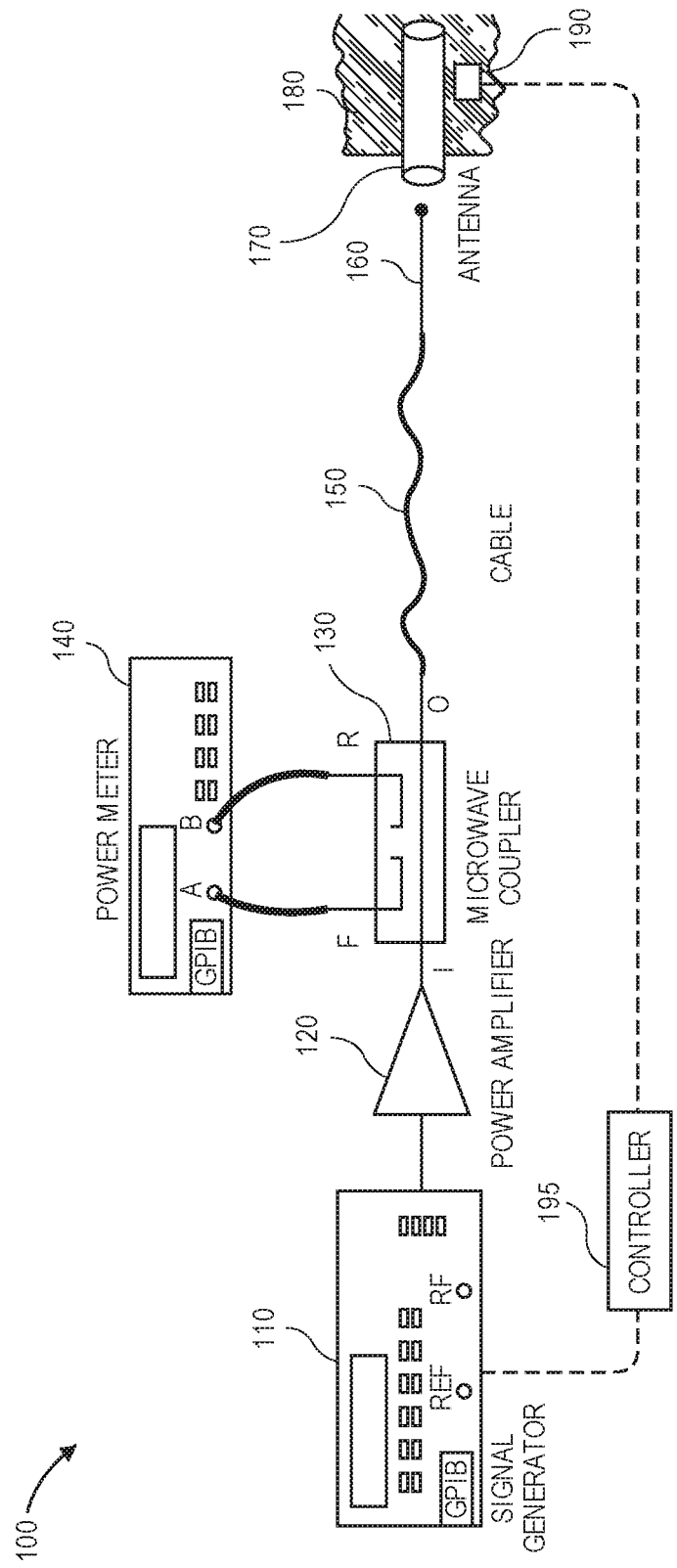
FIG. 1 illustrates an example of a system for decontaminating a tube, according to an embodiment.

Reference will now be made in detail to embodiments, examples of which are illustrated in the accompanying drawings and figures. In the following detailed description, numerous specific details are set forth in order to provide a thorough understanding of the invention. However, it will be apparent to one of ordinary skill in the art that the invention may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the present disclosure. The first object or step, and the second object or step, are both, objects or steps, respectively, but they are not to be considered the same object or step.

The terminology used in the description herein is for the purpose of describing particular embodiments and is not intended to be limiting. As used in this description and the appended claims, the singular forms "a," "an" and "the" are intended to include the plural forms as well, unless the context clearly indicates otherwise. It will also be understood that the term "and/or" as used herein refers to and encompasses any possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Further, as used herein, the term "if" may be construed to mean "when" or "upon" or "in response to determining" or "in response to detecting," depending on the context.

Attention is now directed to processing procedures, methods, techniques, and workflows that are in accordance with some embodiments. Some operations in the processing procedures, methods, techniques, and workflows disclosed herein may be combined and/or the order of some operations may be changed.

The present disclosure is directed to systems and methods for reducing or eliminating microbial biofilms for a number of different applications (e.g., spaceflight, medical, oil and gas, etc.). For example, the present disclosure is directed to systems and methods for reducing or eliminating microbial biofilms for extended space exploration missions using high-frequency microwave energy (i.e., electromagnetic waves) to kill different strains of bacteria, such as *Staphylococcus aureus, Staphylococcus epidermidis, Burkholderia cepacia*, etc., as well as biofilms.

In another example, the microwave energy may be used to decontaminate ports and catheters used in medical patients. The microwave energy may be used to eradicate bacteria without disturbing the tubing with a short exposure duration on the inside of the tubing. As described in more detail below, an antenna may be inserted into the tubing (e.g., catheter) and moved axially within the tubing, and the antenna may radiate microwave energy that eradicates the bacteria. An alternative embodiment may be to build and integrate an antenna into the tubing and then activate the microwave system periodically.

The microwave energy may be directly absorbed by the bacteria, and eradication is caused by thermal heating. In addition, heating of the surrounding healthy tissue is minimal due to the high-frequency (i.e., short wavelength) energy, thereby causing minimal to no damage in terms of cell viability. Based on extensive microwave testing, it is believed that a number of bacterial strains may be substantially eliminated internal and external to the tubing.

FIG. 1 illustrates an example of a system 100 for decontaminating a tube 170, according to an embodiment. The system 100 may include a signal generator 110, a power amplifier 120, a microwave coupler 130, a power meter 140, a cable 150, and an antenna 160. The signal generator 110 may be or include a high-frequency signal generator that may drive the power amplifier 120, which may be a Ka-band amplifier. The amplifier 120 feeds the output signal into the coupler 130, which allows both the forward and reflected power to be continuously monitored.

The output signal may be received by the antenna 160, causing the antenna 160 to generate/emit microwave energy (i.e., electromagnetic waves). A tube (e.g., a catheter or port) 170 may be positioned at least partially within a body 180 (e.g., human or animal tissue and/or fluids). When the antenna 160 is positioned at least partially inside the tube 170, the microwave energy may decontaminate an interior and/or an exterior of the tube 170. In other words, the microwave energy may kill the microbial biofilms that grow on or around the tube 170.

In at least one embodiment, one or more sensors (one is shown: 190) may be coupled to and/or positioned at least partially within the body 180. For example, the sensor 190 may be in contact with the tube 170 or positioned a distance from the tube 170. The distance may be from about 0.1 mm to about 1 mm, from about 0.5 mm to about 2 mm, from about 1 mm to about 3 mm, or from about 2 mm to about 5 mm. The sensor 190 may measure the temperature of the body 180. More particularly, the sensor 190 may measure how much the temperature of the body 180 increases in response to the microwave energy. The sensor 190 may transmit the temperature data to a controller 195, and the controller may control the signal generator 110 in response to the temperature data. For example, if the temperature data indicates that the temperature of the body 180 increases by more than a predetermined amount (e.g., 3° C.), the controller 195 may cause the signal generator 110 to vary the frequency, power, and/or duration of the signals output therefrom to cause the temperature of the body 180 proximate to the tube 170 to decrease again.

For the laboratory tests, three antennas 160 were used: 1) a dielectrically loaded horn, 2) an open-ended waveguide, and 3) a small coplanar antenna.

Microwave Absorption in Catheters/Ports

Tube effects on microwave absorption and antenna detuning were measured for five different types of catheters/ports: 1) endotracheal tubes, 2) urinary catheters, 3) aorta catheters, 4) blood transfer tubes, and 5) special magnesium ribbed catheters. The tube may be aptically transparent. The absorption effects were assessed by measuring the power received with and without the tube present. The tube detuning degradations were determined by measuring the reflected power. The following results were obtained: microwave absorption for all catheters was less than 0.5 dB, which means that less than 10% of the incident power was absorbed. Based on these results, the catheter tubing material should not be an issue.

Temperature Measurements

Test beds using bovine meat were wrapped around the tubing and instrumented with fiber optic sensors (e.g., thermocouples) to record temperature build-up as a function of time. The thermocouples were inserted close to the surface (less than 1/32 inch) and deeper (1/8 inch). The system 100 was operated at 1 watt, 3 watts, and 5 watts.

Figure 2:
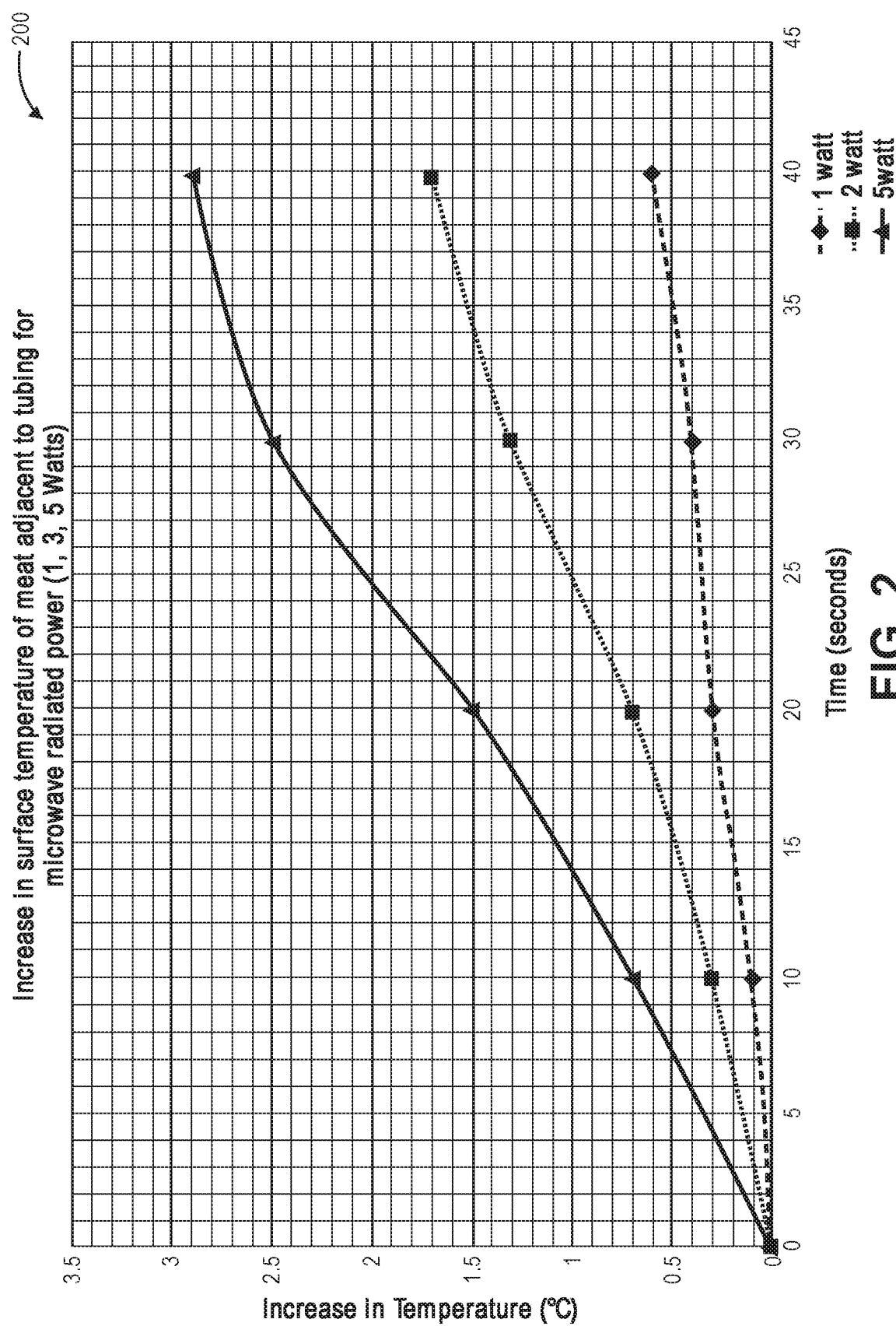
FIG. 2 illustrates a graph showing increases in surface temperature for different power levels, according to an embodiment.

FIG. 2 illustrates a graph 200 showing increases in surface temperature for different power levels, according to an embodiment. As shown in FIG. 2, the maximum temperature increase at the surface of the meat next to the outer surface of the tube was 0.6° C. for one watt of radiated power, 1.7° C. for 3 watts, and 2.9° C. for 5 watts for radiation exposure times of 40 seconds.

Bacteria Tests Using a Sample Catheter

Bacteria ablation (kill) tests were performed to determine representative levels of microwave energy and radiation exposure times for decontaminating tubing (e.g., catheters/ports). Forty microliters of concentrated *Staphylococcus epidermidis* was placed in sterile 50 ml vials. For each exposure, a vial was placed behind a cut section of a sample catheter and exposed to microwave energy for 60 seconds. Two microwave power levels were used: three tests with 3 watts of energy and two tests with 10 watts of energy. The radiated samples were diluted 1:100, streaked on blood agar plates, and incubated. Colony-forming units were enumerated, and the counts shown below are as follows:

TABLE 1

| Sample Number | Power | Colonies | Survival |
| --- | --- | --- | --- |
| Control Sample | | 1379 colonies | 100% survival |
| Sample 1 | 3 watts | 1 colony survived | 99.9% dead |
| Sample 2 | 3 watts | 1 colony survived | 99.9% dead |
| Sample 3 | 3 watts | 4 colony survived | 99.7% dead |
| Sample 4 | 10 watts | 1 colony survived | 99.9% dead |
| Sample 5 | 10 watts | 5 colony survived | 99.6% dead |

Hundreds of bacterial tests were performed using directed microwave energy. The parameters include microwave power, forward and reflected power, and exposure time, which were varied to determine bacterial kill rates. Although test beds varied depending on the application, (e.g., space suit tubing, bacteria embedded in various models) from those that will be required for catheter/port models, tests results obtained may provide insight into what may be expected.

Figure 3:
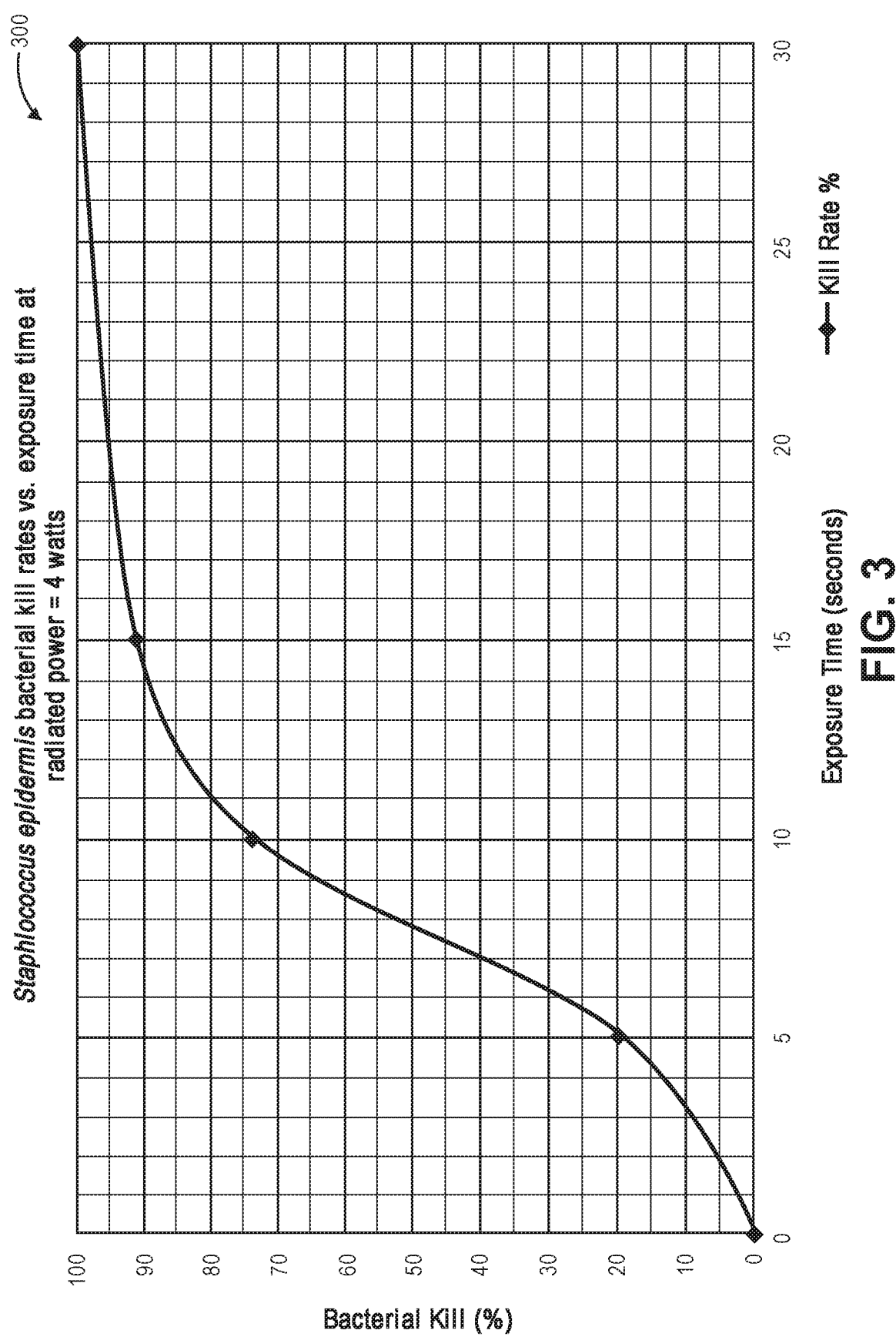
FIG. 3 illustrates a graph showing bacterial kill rates versus time, according to an embodiment.

FIG. 3 illustrates a graph 300 showing bacterial kill rates versus time, according to an embodiment. In one test, the bacteria used was *Staphylococcus epidermidis*. The radiated power was at 4 watts. The antenna was an open-ended waveguide. Radiated samples were diluted 1:00, streaked on blood agar plates, and incubated. Colony-forming units were counted and compared to control.

TABLE 2

| Exposure time (seconds) | Ablation (% kill) |
| --- | --- |
| 0 | 0 |
| 5 | 19 |
| 10 | 75 |
| 15 | 91 |
| 30 | 100 |

In another test, the bacteria used was *Burkholderia cepacia*. The radiated power was at 6 watts. The antenna was a horn antenna. Bacteria were placed in a single droplet into a 60 mm sterile petri dish. After exposure, samples were diluted 1:00 and streaked on plates and incubated at 37° C. Colonies were later counted.

TABLE 3

| Exposure time (seconds) | Ablation (% kill) |
| --- | --- |
| 15 | 68.0 |
| 30 | 85.0 |
| 30 | 97.0 |
| 45 | 99.4 |
| 60 | 99.8 |

Conclusions

All samples of catheters and ports that were tested show no degradation from the penetrating microwave signals. The expected temperature rise of the body tissue should be less than 2.5° C. for the power levels and exposure times required for decontamination of catheters/ports. Bacterial kills of 95%-100% may be expected for radiation exposures of approximately 30 to 45 seconds.

Microwave Absorption Tests to Measure Penetration Depth into Healthy Tissue

The penetration depth into meat is less than about 1 mm (e.g., about 0.6 mm) for the Ka-band energy (e.g., 26.5 GHz to 40 GHz). Thus, the natural body fluids surrounding a catheter may protect the healthy tissue from being exposed to harmful microwave energy. The biofilm may be heated quickly while not allowing thermal conduction to be an active heating mechanism.

Kill Rates for Planktonic Bacteria in Solution

A series of ablation (kill) tests were performed for *Staphylococcus aureus* planktonic bacteria in 30 μL and 100 μL at radiated powers of 3.0 and 3.6 watts. Results indicated kill rates of 44%, 88%, and 99% at temperature of 120° F., 140° F., and 160° F. Times varied up to 60 seconds.

Comparison of Microwave Energy Absorption of Biofilms in Water Compared to Energy Absorption in Water Only There is a small increase in temperature over time due to the presence of biofilms. The biofilm may interact directly with the incoming microwave energy, thereby absorbing the energy and heating the bacteria. This phenomenon may also serve to protect the surrounding healthy tissue.

Comparison of Microwave Heating and Water Bath Heating for Bacterial Kill

Results indicate a direct microwave heating temperature threshold that is much lower than the temperature threshold for water bath bacteria killing. These unexpected results emphasize that high frequency microwave energy should be a good option to use for the ablation mechanism.

Low Microwave Power Tests with Longer Exposure Times

These tests used low microwave powers (e.g., 0.5 W, 1.0 W, and 1.5 W) at longer exposure times to determine the efficiency of killing bacteria at lower power levels. An unexpected result was that total energy (i.e., power×time) is not a good criteria for evaluating the efficiency of a system. Higher power and shorter radiation times provide much better performance for bacterial ablation.

Differences in Microwave Absorption Between Biofilms and Planktonic Bacteria

Test results indicate the dense inter-structure of biofilms absorbs incident microwave energy. This should aid in localizing the absorption of microwave energy to the near outside of the tubing (e.g., catheter) wall. The existence of fluid within the biofilm is also an advantage in localizing the tissue heating.

Alternate antenna configurations may include antennas that are slideable through the catheters, antennas built into the catheter's tubing, array antennas, and other configurations.

1. Microwave Absorption Tests to Measure Penetration Depth into Healthy Tissue

When exposing the bacteria and biofilms to microwave energy, the radiation absorption may be increased in the bacteria and minimized in the adjacent healthy human tissue. This can be done by selecting microwave frequencies (short wavelength) that limit penetration depth of the energy. As the energy penetrates into the bacteria, surrounding bodily fluids, and the adjacent tissue, the energy is absorbed primarily by fluid in the surrounding environment. The penetration depth of the particular microwave energy is defined as the distance at which the energy is reduced to $(1/e)^2$ or $1/7.4$ of the value at the surface, which is about 9 dB down.

In the Ka-band microwave region, the wavelength is about 10 mm. The penetration depth is less than 10% of the wavelength, or less than 1 mm. Thus, greater than about 75% (e.g., about 90%) of the microwave energy may be absorbed within 1 mm of the surfaces of the tubing (e.g., catheter). As this energy is absorbed, the surrounding medium (e.g., fluid and tissue) will be heated. This heating will spread due to thermal conduction within the medium. The thermal heating, and hence the ablation of bacteria and biofilm, may be limited to short exposure time periods. The heating through thermal conduction can then be limited to regions adjacent to the catheter surfaces.

Tests were conducted to determine the penetration depths of Ka-band energy into watery fluids and tissue (e.g., meat). It will be shown later that watery fluids and biofilms immersed in watery fluids have similar microwave absorption characteristics. For the absorption tests to measure representative penetration depths, a Ka-band (e.g., 30 GHz) signal radiated through a clear plastic dish with a 2 inch diameter. The radiating antenna was a 0.5 inch by 0.7 inch horn, and the receiving antenna was a 3.97 inch by 3.97 inch horn. The received power was measured with a number of different mediums in the plastic dish and compared to the power received through the dish only. The difference in received power is the power absorbed by the medium in the dish. Both forward and reflected power were monitored to ensure the microwave energy was not reflected. Table 4 below shows the results.

TABLE 4

| Medium | Energy Amount of Absorption by Medium only | Calculated Penetration Depth of Energy into Medium |
| --- | --- | --- |
| 2 mm of water | 25.4 dB | 0.635 mm |
| 1.7 mm of ham | 22.4 dB | 0.63 mm |
| 0.6 mm of roast beef | 15.9 dB | 0.33 mm |
| 1.2 mm of roast beef | 23.9 dB | 0.44 mm |

These results indicate the penetration depth is about 6% of the Ka-band wavelength or about 0.6 mm, depending upon the water content within the tissue. The optimal heating mechanism for killing biofilms while not damaging the healthy tissue may be to heat the biofilm quickly and not allow thermal conduction to play an active role in surrounding tissue. Because of the high frequency, short wavelength, of the system 100, the naturally occurring body fluids around the catheter protect the adjacent healthy tissue.

2. Kill Rates for Planktonic Bacteria in Solution

When optimizing the microwave parameters (e.g., exposure time, radiated power, temperature, frequency, etc.), the user should know the behavior of biofilms, as well as planktonic bacteria, in response to high frequency microwave radiation. For the planktonic bacteria, a series of tests were performed to measure the ablation (kill) rate as a function of fluid temperature. Similar tests were performed to ascertain the response of biofilms versus temperature.

In one test, as shown in Table 5, 30 µL of *Staphylococcus aureus* planktonic bacteria in microfuge tubes was radiated with 3.0 watts of power. In another test, as shown in Table 6, 100 µL of *Staphylococcus aureus* planktonic bacteria was radiated with 3.6 watts of power. The exposure times were varied for each radiation condition, and the temperatures were measured in calibration tests using a thermal imager with an intensity setting for 0.88. Three test runs were made for each time setting.

TABLE 5

| Time | Temperature | Kill Rate |
| --- | --- | --- |
| 12 seconds | 125° F. | 43% |
| 17 seconds | 143° F. | 82% |
| 25 seconds | 158° F. | 99% |
| 40 seconds | 180° F. | 99.9% |

TABLE 6

| Time | Temperature | Kill Rate |
| --- | --- | --- |
| 20 seconds | 116° F. | 44% |
| 30 seconds | 133° F. | 93% |
| 45 seconds | 155° F. | 100% |
| 60 seconds | 173° F. | 100% |

Figure 4:
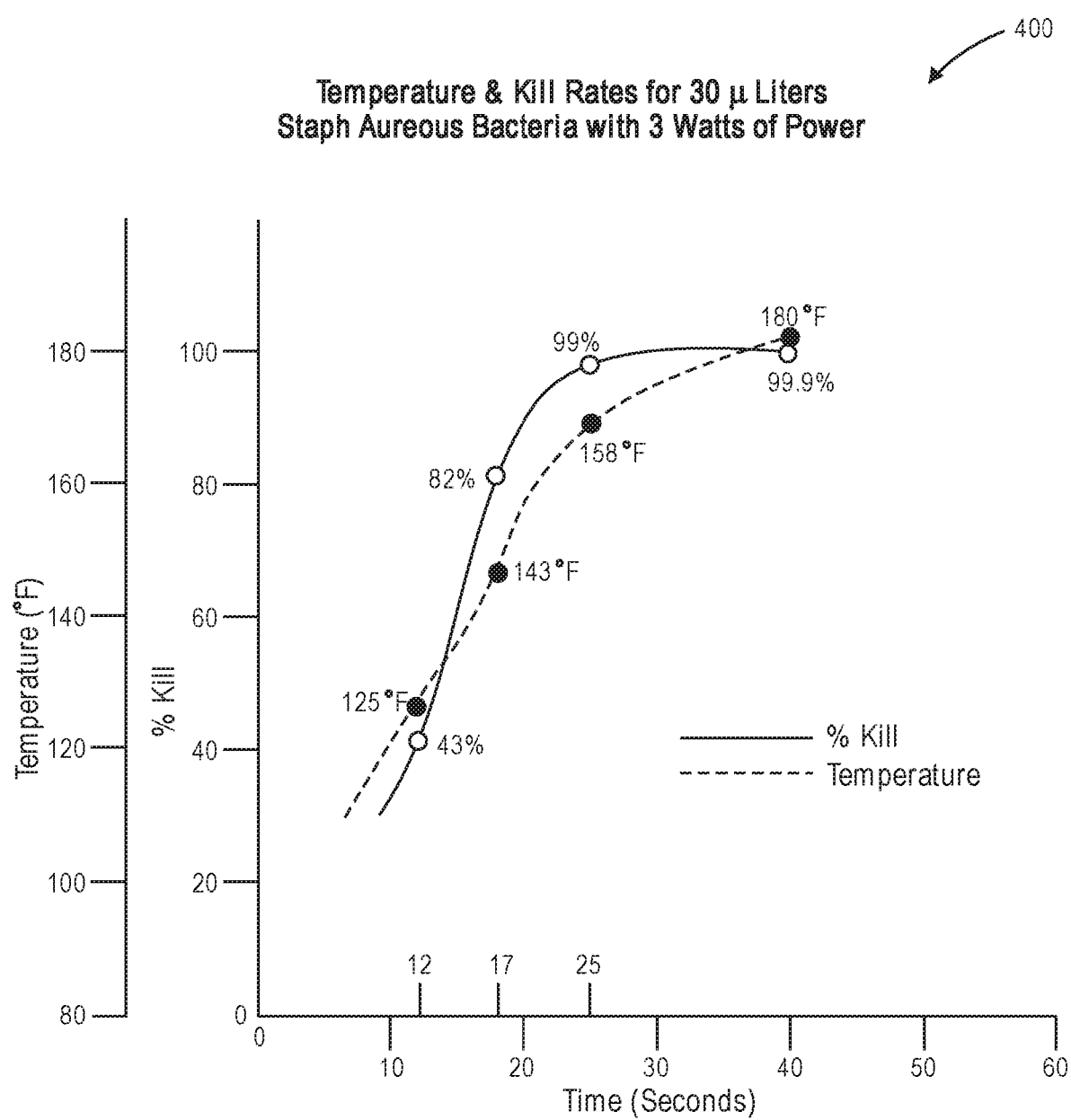
FIG. 4 illustrates a graph showing temperature and kill rates for 30 µL of *Staphylococcus aureus* planktonic bacteria with 3 watts of power, according to an embodiment.

FIG. 4 illustrates a graph 400 showing temperature and kill rates for 30 µL of *Staphylococcus aureus* planktonic bacteria with 3 watts of power, according to an embodiment.

Figure 5:
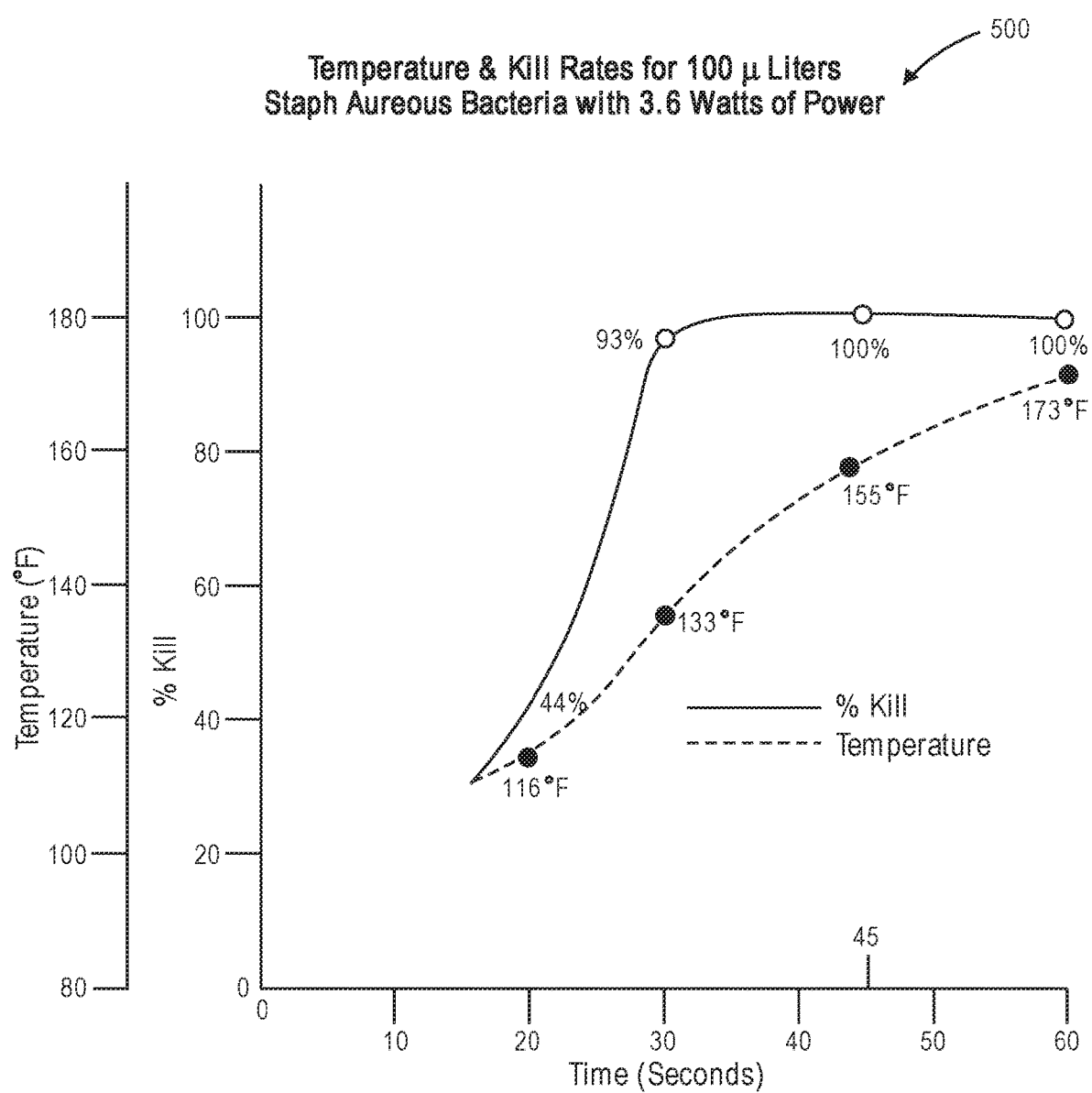
FIG. 5 illustrates a graph showing temperature and kill rates for 100 µL of *Staphylococcus aureus* planktonic bacteria with 3.6 watts of power, according to an embodiment.
Figure 6:
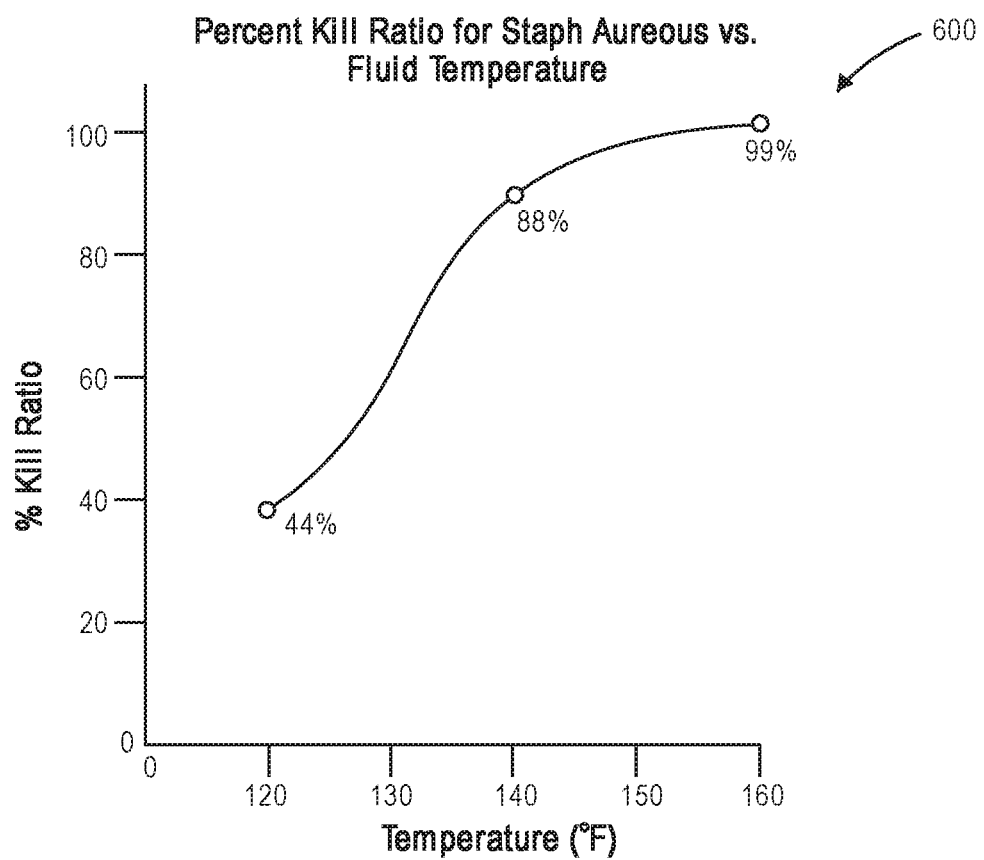
FIG. 6 illustrates a graph showing the percent kill ratio for *Staphylococcus aureus* planktonic bacteria vs. fluid temperature, according to an embodiment.

FIG. 5 illustrates a graph 500 showing temperature and kill rates for 100 μL of *Staphylococcus aureus* planktonic bacteria with 3.6 watts of power, according to an embodiment. FIG. 6 illustrates a graph 600 showing the percent kill ratio for *Staphylococcus aureus* planktonic bacteria vs. fluid temperature, according to an embodiment. The data shown is for planktonic bacteria in a fluid. However, later tests indicated the interactive lattice within the biofilm tended to absorb more of the microwave energy radiating through and produced more localized heating.

3. Microwave Energy Absorption of Biofilm in Water Compared to Energy Absorption in Water Only Ideally most of the radiated microwave energy would be absorbed by the biofilm, which is attached to the tube (e.g., catheter). Subsequently, there may be thermal conduction of this heat generated near the catheter surface by the absorbed energy throughout the fluid. There may be additional heat generated at the catheter's surface by the additional energy absorbed in the biofilm.

Tests were conducted to measure the temperature increases as a function of time in fluids, with and without biofilms. A small thermocouple placed at the bottom of a plastic well containing the fluid provided the most accurate temperature measurements. Proper placement of the thermocouple within the biofilm allowed a direct measurement of the microwave energy absorbed in that region. This heat is thermally conducted throughout the fluid; however, the thermal measurement taken adjacent to or within the biofilm provides insight into the heating taking place at the outer surface of a catheter. For the tests, 100 μL and 200 μL fluid samples with and without biofilms were used, with radiated microwave powers of 2.57 W, 3.3 W, and 4.17 W. Exposure times selected were less than 60 seconds.

The tests using 200 μL gave consistent results while the 100 μL samples varied. The surface tension of the 100 μL fluids within the wells may have produced small variations in the fluid thickness for the exposure times of 30 seconds and 45 seconds:

TABLE 7

Conditions: 100 μL, P = 2.5 W

| Time | Run 1 | Run 2 | Run 3 | Run 4 |
|---|---|---|---|---|
| 30 Sec | 120° F. | 114° F. | 114° F. | 118° F. |
| 45 Sec | 137° F. | 129° F. | 130° F. | 134° F. |

TABLE 8

Conditions: 200 μL, P = 2.5 W

| Time | Run 1 | Run 2 | Run 3 | Run 4 |
|---|---|---|---|---|
| 30 Sec | 110° F. | 110° F. | 110° F. | 110° F. |
| 45 Sec | 124° F. | 124° F. | 124° F. | 125° F. |

Thus, for the biofilm ablation tests as a function of temperature, 200 μL fluid samples were used. The 200 μL fluids have a depth of 6 mm within the plastic wells. The biofilms are grown at the bottom of a well, and the fluid fills the well to a depth of 6 mm. The microwave antenna is beneath the well radiating upward through the biofilm and fluid.

To determine the microwave absorption rate within the biofilm at the bottom of a well, multiple tests were performed to ensure statistically accurate heating results. Based upon previous ablation tests for planktonic bacteria, a radiated power of 4.17 W into 200 μL of biofilm plus fluid was chosen to ensure a wide range of temperatures at times of 45 seconds or less.

Figure 7:
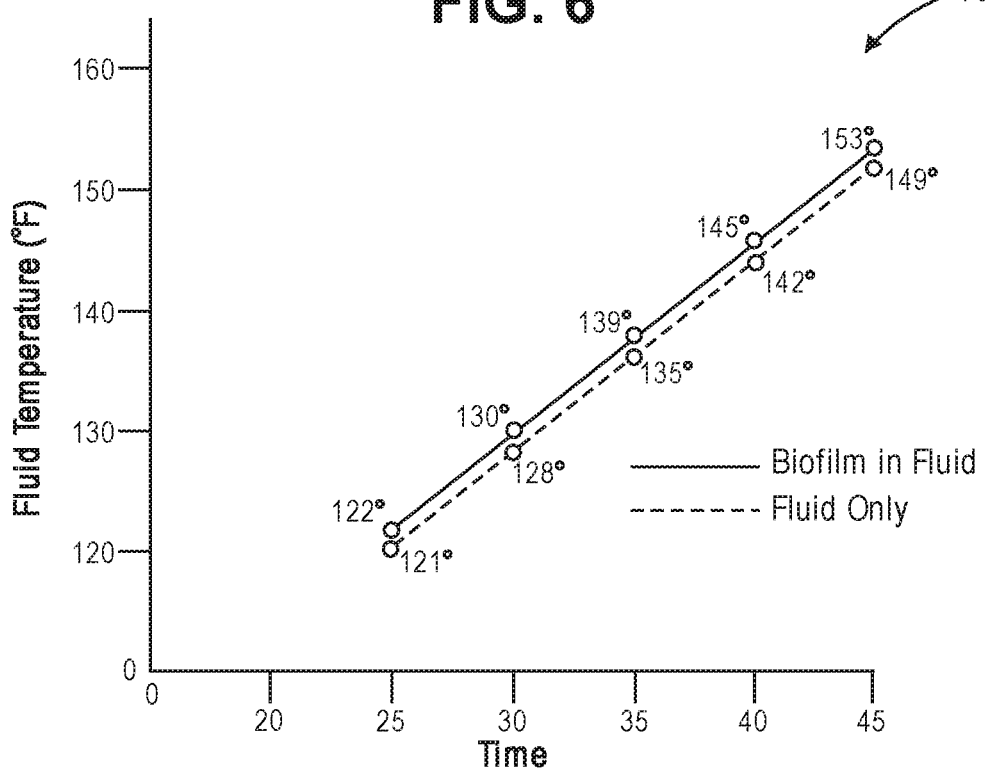
FIG. 7 illustrates a graph showing fluid temperature vs. time, according to an embodiment.

FIG. 7 illustrates a graph 700 showing fluid temperature vs. time, according to an embodiment.

Conclusions from these tests:

1. A radiated power of 4.17 W provides a good range of temperatures for the ablation tests.
2. There is a 2° F. increase in fluid temperature at a specific time interval when the biofilm is in the fluid as compared to fluid only. This small increase was consistent for a large number of tests.
3. This temperature increase was also present in similar tests when the power radiated was 2.57 W and 3.3 W. The biofilm is theorized to interact directly with the microwave energy, thereby producing energy absorption and a resultant additional heating of the fluid within the biofilm. The effect could aid in localizing the heating to the surfaces near the catheter and thereby, shielding the healthy tissue away from the catheter.
4. Comparison of Microwave Heating and Water Bath Heating for Bacteria Kill There may be two heating mechanisms for the bacteria, which are: (1) direct absorption of the high frequency microwave energy by the bacteria, and (2) indirect absorption where the water absorbs microwave energy, thereby heating the water followed by conduction heating from the water to the bacteria.

Since the microwave penetration depth for Ka-band energy is less than 1 mm within fluids, larger volumes of fluids may enhance indirect absorption. From a medical point of view, direct absorption has several advantages over indirect absorption: (1) the radiation damage to surrounding healthy tissue can be minimized since the bacteria is absorbing more energy, and (2) the exposure time can be shorter, thereby reducing conduction heating into the surrounding tissues.

These tests were designed to measure differences in direct and indirect absorption by comparing results from microwave heating with heating by conduction only. Heating by thermal convection can be achieved by using water bath heating of the bacteria. In this configuration, there is no microwave energy present to kill the bacteria. For the microwave heating tests, the conditions include: (1) small amount of fluids containing planktonic bacteria (e.g., 100 μL), (2) short exposure times to minimize thermal conduction (e.g., 20 seconds and 30 seconds), and (3) relatively high microwave power e.g., (3.6 watts).

The temperature of the 100 μL fluids was first measured as a function of time, up to 20 and 30 seconds. Then, the same temperature profile (i.e. temperature versus time) was matched by precisely controlled preheated water baths. The vials filled with 100 μL of bacterial fluids will have approximately the same heating profiles over the same time periods. A water bath temperature of 188° F. was found to produce a very similar temperature profile as the microwave heated vials.

Figure 8:
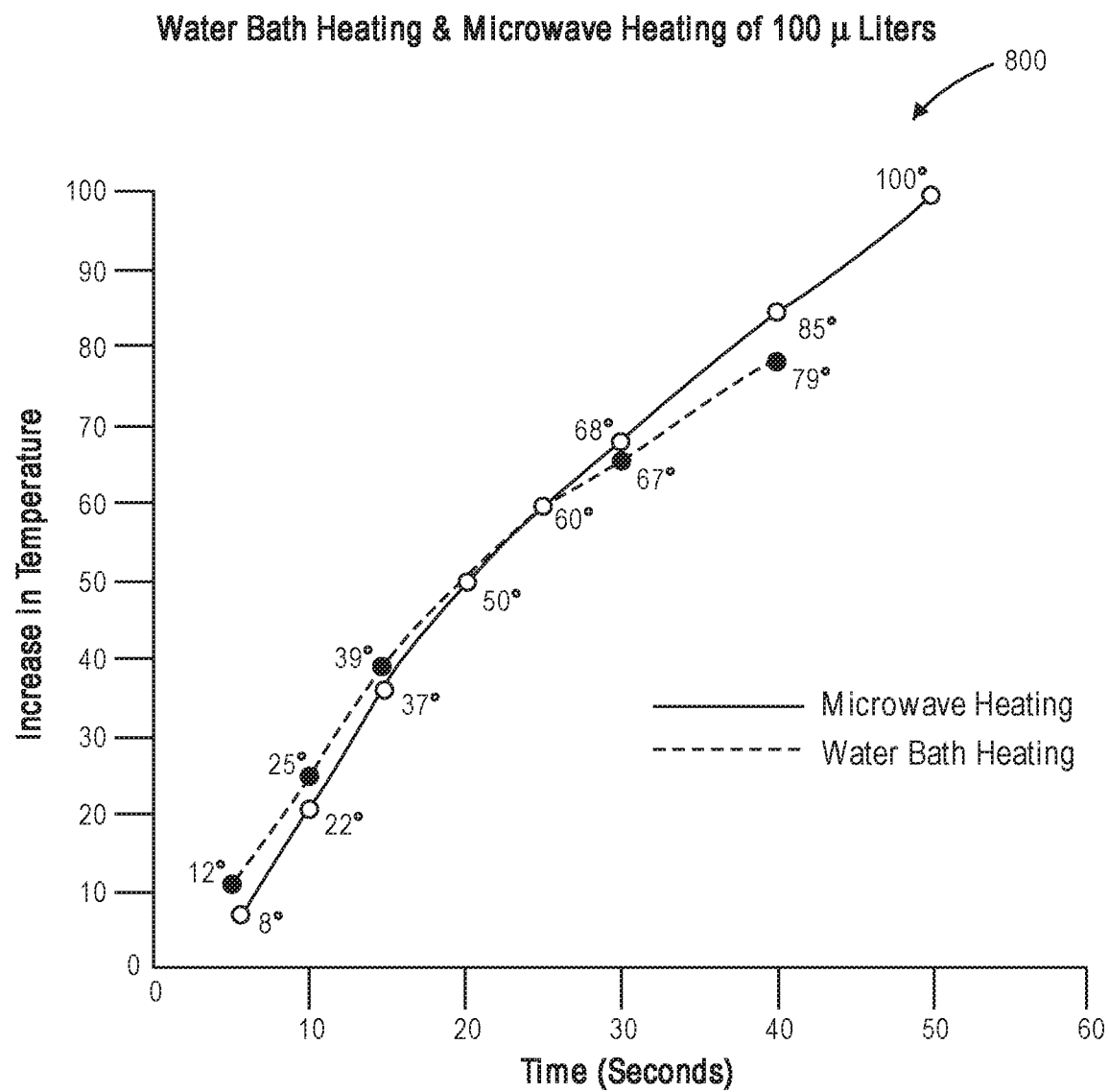
FIG. 8 illustrates a graph showing water bath heating and microwave heating of 100 µL of fluid, according to an embodiment.
Figure 9:
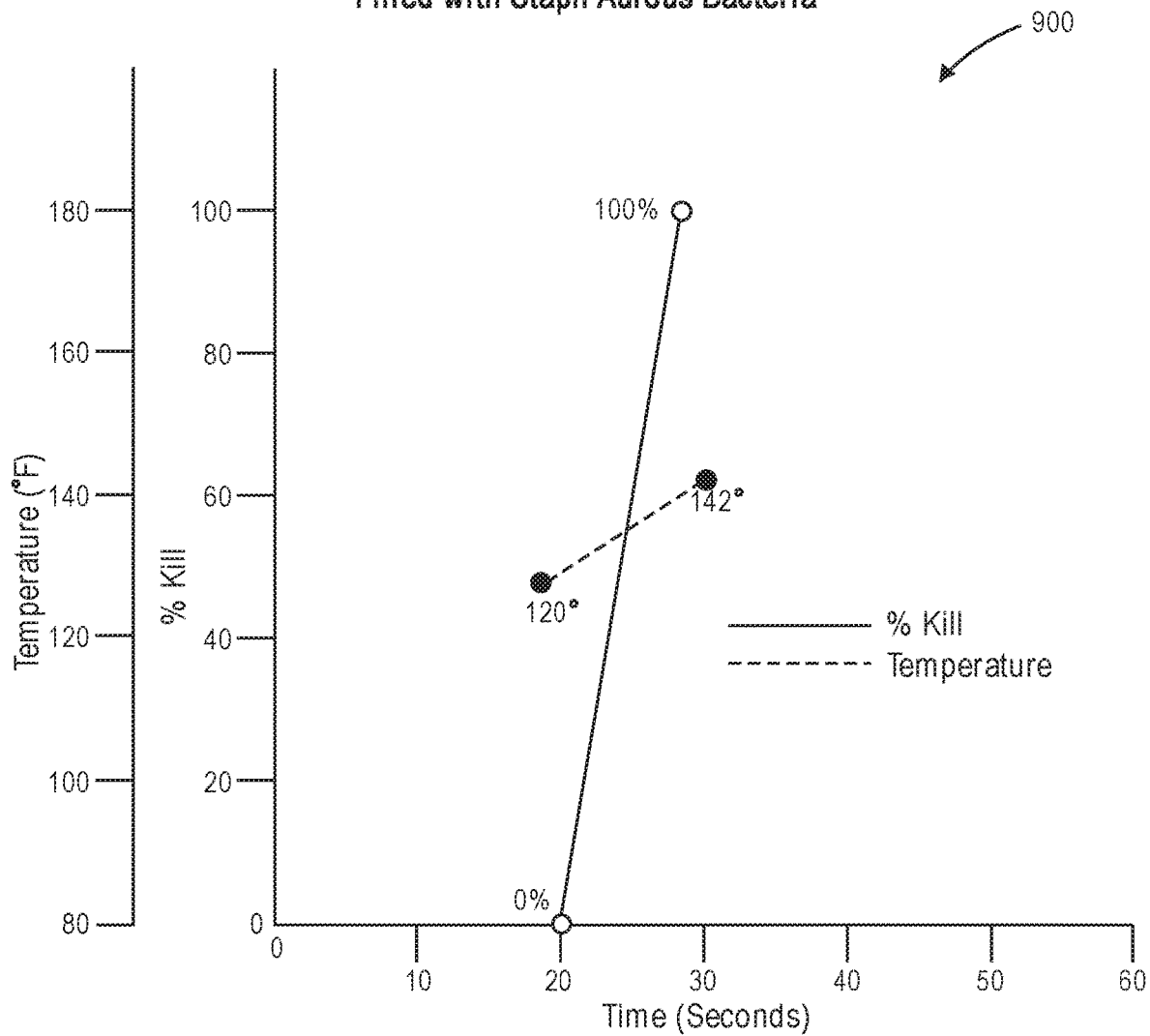
FIG. 9 illustrates a graph showing water bath heating and percent kill for 100 µL vials filled with staph aurous bacteria, according to an embodiment.
Figure 10:
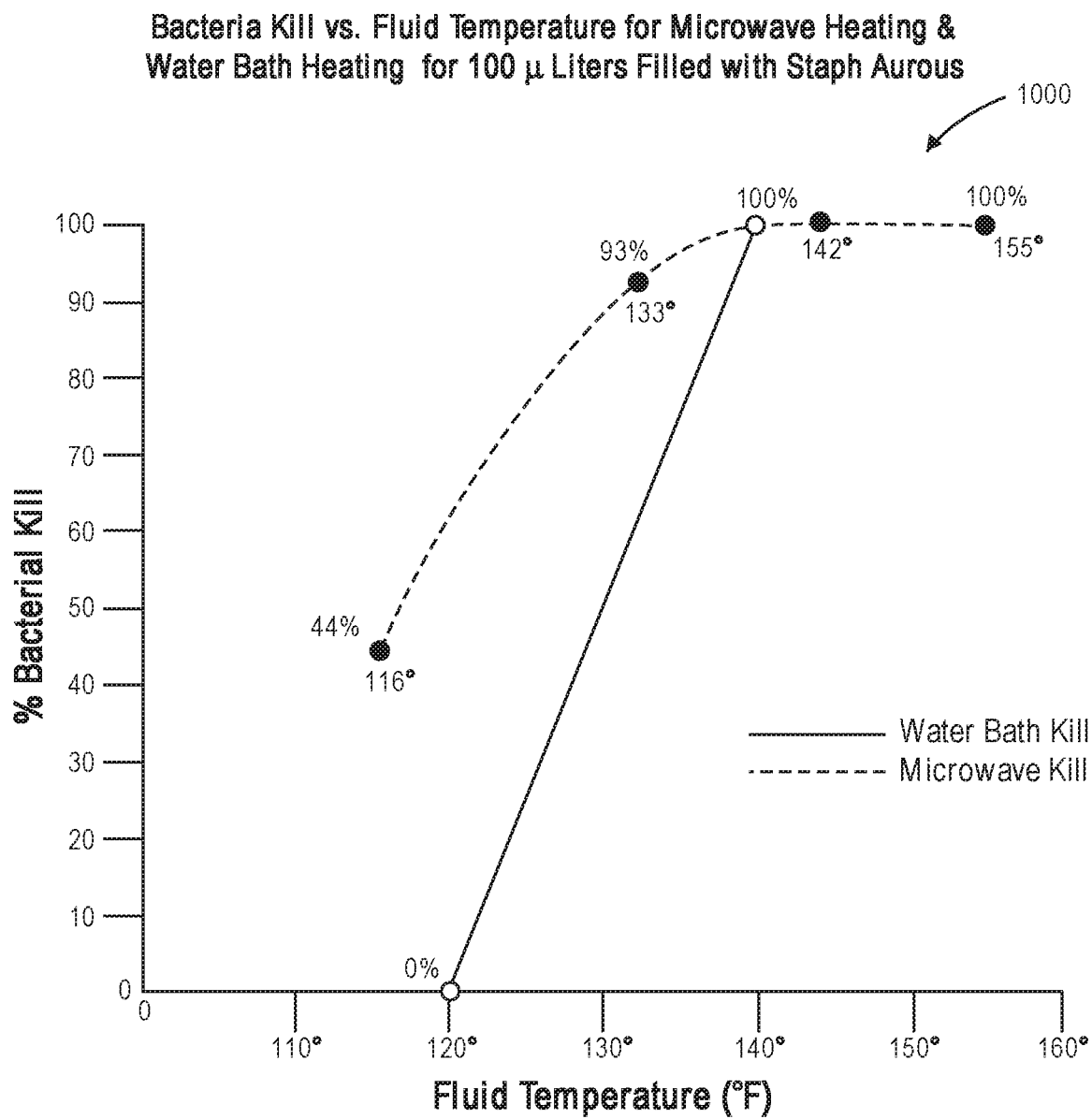
FIG. 10 illustrates a graph showing bacteria kill vs fluid temperature for microwave heating and water bath heating for 100 μL vials filled with staph aurous bacteria, according to an embodiment.

FIG. 8 illustrates a graph 800 showing water bath heating and microwave heating of 100 μL of fluid, according to an embodiment. FIG. 9 illustrates a graph 900 showing water bath heating and percent kill for 100 μL vials filled with *Staphylococcus aureus*, according to an embodiment. By replotting the same data in the form of bacterial kill versus fluid temperature, the differences between microwave heating of the water and bacteria and conductive heating through water (with no microwave radiation) can be seen. FIG. 10 illustrates a graph 1000 showing bacteria kill vs fluid temperature for microwave heating and water bath heating for 100 µL vials filled with *Staphylococcus aureus*, according to an embodiment.

There appears to be a temperature threshold (>120° F.) before thermal killing of bacteria occurs due to conduction heating from the water. The temperature threshold is much lower for microwave heating (see FIG. 9 at the 20 second mark). This is an unexpected result, which emphasizes that very high frequency microwave energy may be used, which the bacteria readily absorbs.

5. Low Microwave Power Tests with Longer Exposure Times

Low power (0.5 W, 1.0 W, 1.5 W) microwave tests were used to determine percent kill for several types of bacteria at relatively low temperatures for long periods of time (e.g., 45 seconds to 200 seconds). The tests were also used to determine kill rates for microwave heating of the bacterial fluids as compared to non-microwave heating of the bacterial fluids (i.e. with heated water only).

Figure 11:
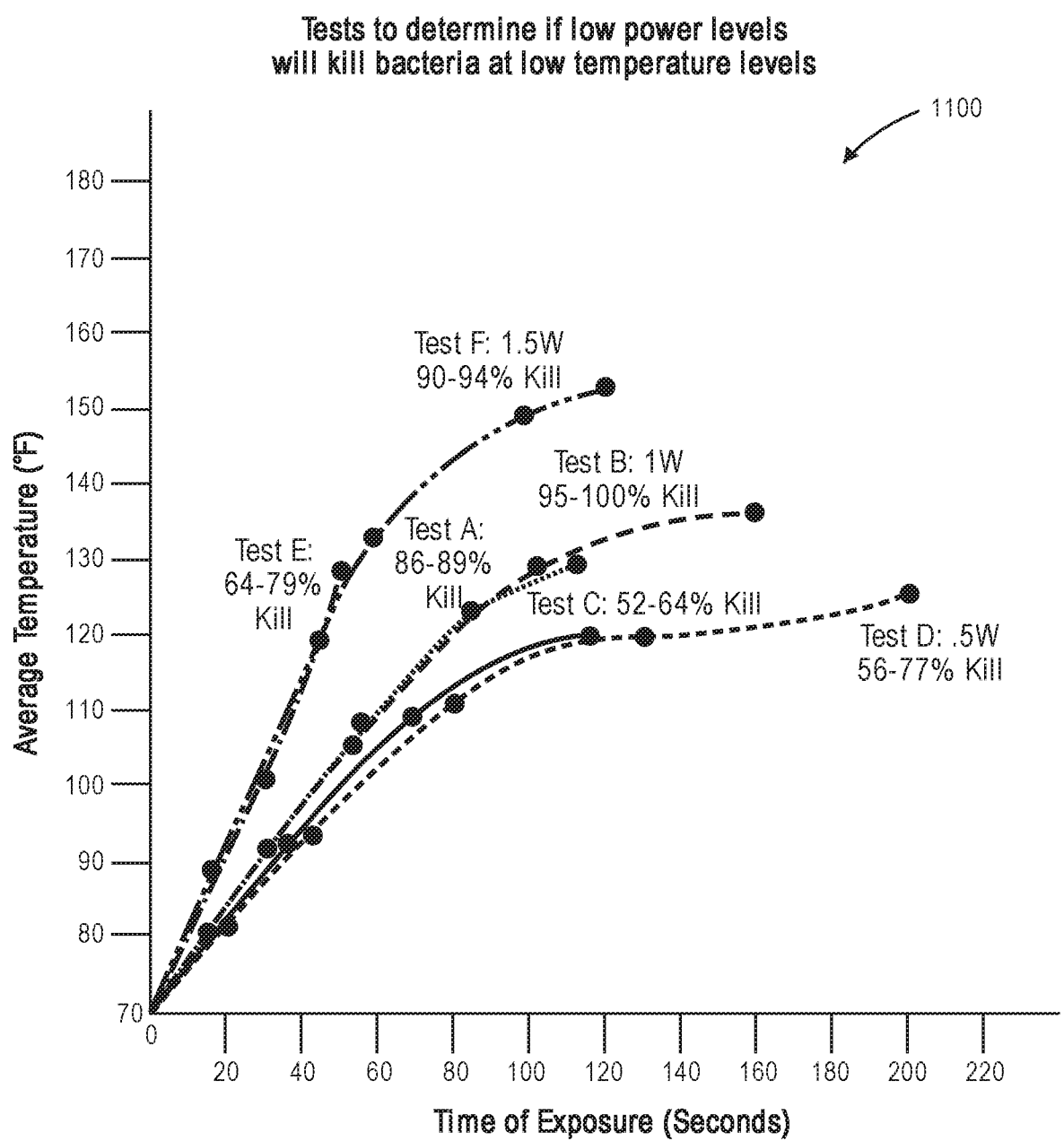
FIG. 11 illustrates a graph showing tests to determine if low power levels will kill bacteria at low temperature levels, according to an embodiment.

FIG. 11 illustrates a graph 1100 showing tests to determine if low power levels kill bacteria at low temperature levels, according to an embodiment. These results are only for small bacterial colonies. The temperatures of the 20 µL fluids were measured in a closed vial with a thermal imager at 5 second time intervals. The heating curves were well-behaved, and all tests indicated thermal equilibrium was achieved at varying temperatures depending upon the amount of input microwave power. Relatively low microwave powers (e.g., 0.5 W to 1.5 W) were used to examine the characteristics of bacteria kill versus temperature and exposure time. The kill rates are shown for different temperature (of the fluid) ranges.

TABLE 9

| Temperature Range | % of Bacteria Kill | Exposure Times & Wattage |
|---|---|---|
| 120° F.-130° F. | 52%-79% | 45 sec-200 sec at .75 W and 1.5 W |
| 130° F.-140° F. | 85%-100% | 110 sec-170 sec at 1 W |
| 140° F.-155° F. | 90%-95% | 120 sec at .5W |

In Table 9, higher wattage (1.5 W) kills more effectively and quicker (at ¼ of the time) than lower wattage (0.75 W). There are minimal benefits in increased bacterial kill rates after thermal equilibrium is attained (where the heating curve versus time flattens). For most applications, optimal kill performance may be achieved with higher power and shorter exposure times, rather than lower powers and longer exposure times. In other words, total energy (i.e., power× time) is not a good criteria for evaluating a system. These results are consistent with previous computer simulations for another microwave ablation system in which optimal kill results were achieved by maximizing microwave radiation effects while minimizing thermal conduction into tissue.

While the precise wattage levels and exposure times may vary according to the particular bacteria being exposed, the conclusions are the same. The direct high frequency microwave energy should be the primary killing mechanism rather than the indirect mechanism of heating the fluid/tissue environment which then transfers heat to the bacteria. Radiating the bacteria with relatively high power and short exposure times may minimize thermal conduction effects and limit the heating region at this short operating wavelength.

6. Differences Between Microwave Absorption by Biofilms and Planktonic Bacteria

Biofilms can be characterized as bacteria interwoven together by a sticky-looking substance including polysaccharides. A biofilm can be dense, interwoven, and helps to protect the bacteria from outside destructive mechanisms. Biofilms are usually more difficult to kill than ordinary bacteria. However, this dense bacterial barrier can be of help in microwave ablation.

Tests were performed to compare microwave absorption by biofilms with absorption by water only. The biofilms were grown in individual round plastic wells, with a 0.64 $cm^2$ bottom area and 1 cm depth. The biofilm grew to a thickness of less than 0.7 mm, which covered the bottom of an individual well. Water was injected to a depth of 1 mm (which is slightly more than the penetration depth of the microwave signal) and also to a depth of 6 mm.

There are two killing mechanisms of the bacteria with the biofilm. First, there is direct absorption of the microwave energy by the biofilm. The killing time can be 10 to 15 seconds depending upon the amount of radiated power (e.g., less than 3 watts). Second, there is microwave power absorption by the surrounding fluid, which heats the fluid. These two effects combine to kill the bacteria.

The microwave energy absorbed by the biofilm does not appear to substantially heat the surrounding fluid. After the bacteria is killed, the portion of the incident energy that was absorbed by the biofilm then goes into heating the surrounding fluid.

The power absorption of the bacteria/fluid interaction proves an inherent level of protection to the surrounding healthy tissue. This bacteria/fluid interface protects the healthy tissue by creating a barrier that effectively attenuates the microwave energy. This barrier is most effective at predetermined frequencies. The healthy tissue becomes more transparent at lower frequencies (i.e., longer wavelengths).

Figure 12:
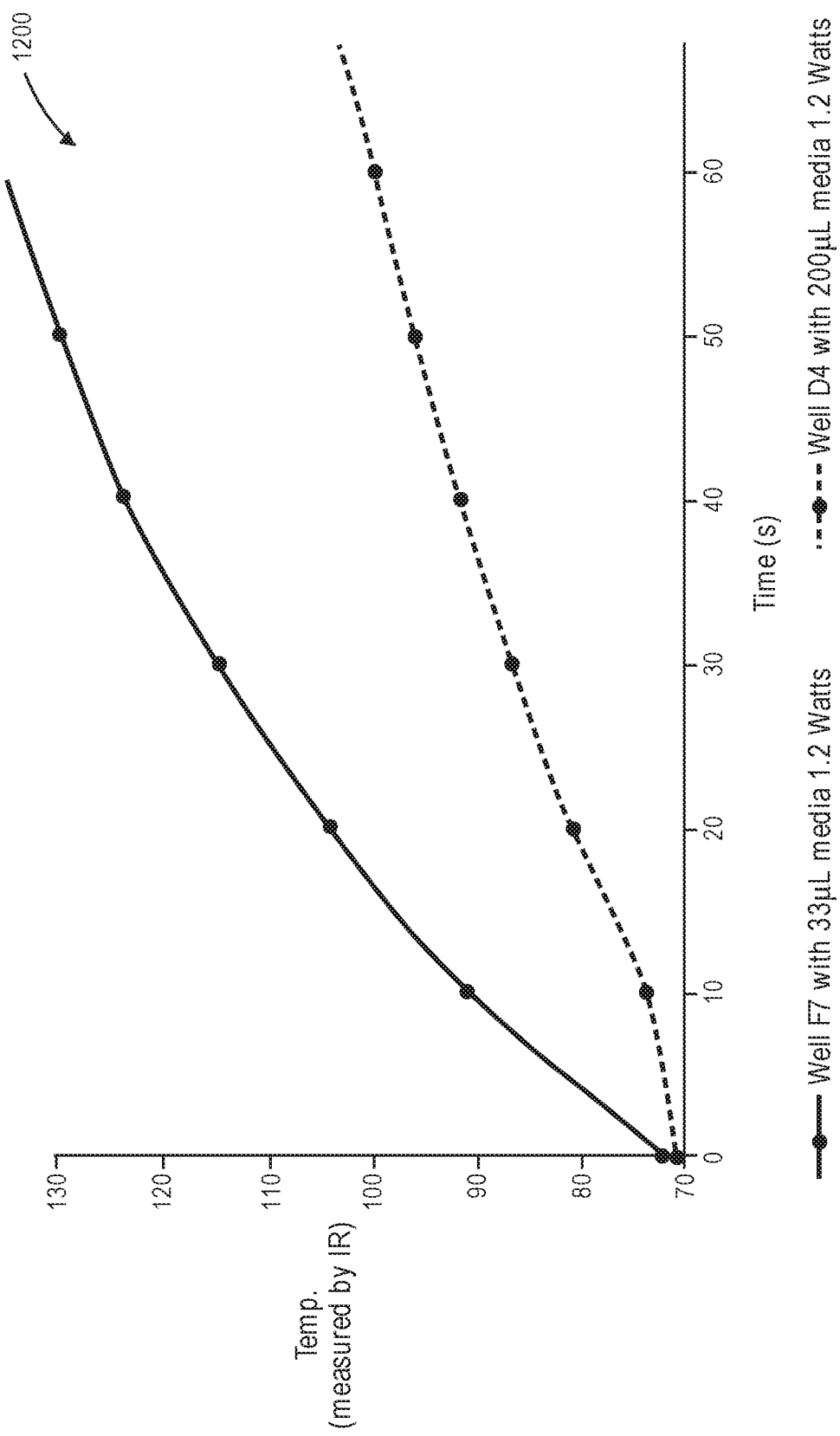
FIG. 12 illustrates a graph showing the effects of microwave energy absorption by biofilm in 200 micro liters of media, according to an embodiment.

The parameter measured to represent microwave absorption was surface temperature as measured by an infrared thermal imager. FIG. 12 illustrates a graph 1200 showing the effects of microwave energy absorption by biofilm in 200 µL of media, according to an embodiment. The results shown in FIG. 12 indicate a strong initial microwave absorption by the biofilm. This unexpected result is in contrast to hydrated bacteria only which shows little microwave absorption. The dense understructure of the biofilms may absorb the incident microwave energy.

7. Alternate Antenna Configurations Include Antennas Slideable Through the Catheters, Antennas Built into the Catheter's Tubing, Array Antennas, and Other Configurations.

Figure 13:
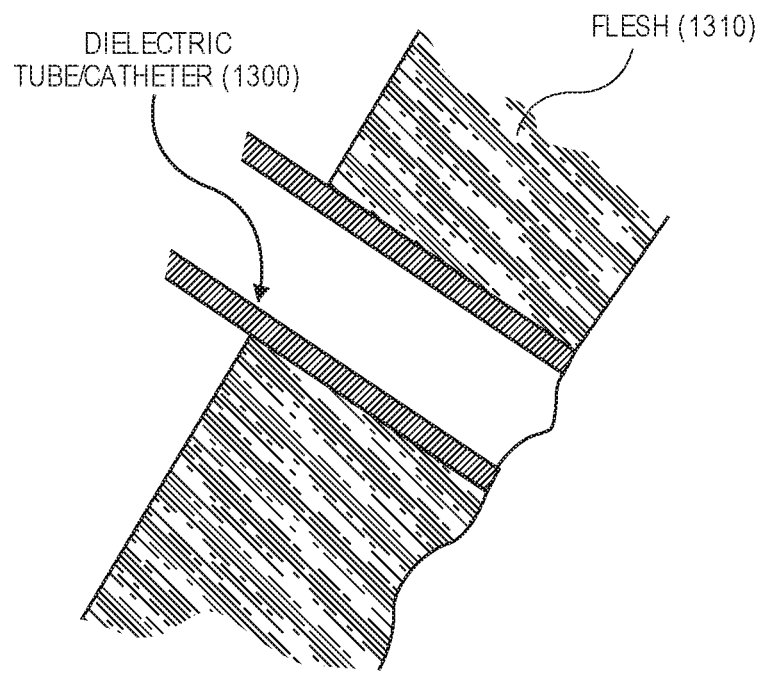
FIG. 13 illustrates a schematic side cross-sectional view of a tube (e.g., a port) with dielectric walls inserted into flesh, according to an embodiment.
Figure 14:
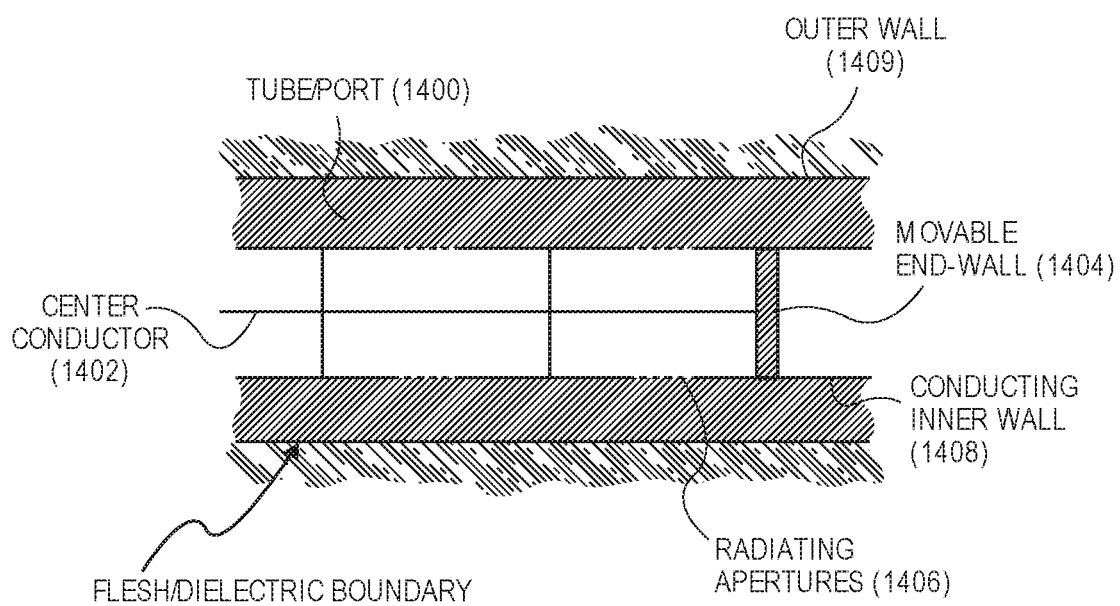
FIG. 14 illustrates a schematic side cross-sectional view of another tube (e.g., a port) with a radiating center conductor acting as an antenna, according to an embodiment.

FIG. 13 illustrates a schematic side cross-sectional view of a tube (e.g., a port, catheter, etc.) 1300 with dielectric walls inserted into flesh 1310, according to an embodiment. The tube 1300 is positioned at least partially within the flesh 1310 (e.g., tissue and fluids). FIG. 14 illustrates a schematic side cross-sectional view of another tube (e.g., a port) 1400 with a radiating center conductor acting as an antenna, according to an embodiment. In FIG. 14, the inner surface 1408 of the tube 1400 is electrically-conducting at the frequencies of operation. A center conductor 1402 attached to a movable end-wall 1404 passes through the tube 1400. Radiating apertures 1406 in the conducting inner surface 1408 enable electromagnetic energy (i.e., waves) to escape (e.g., leaky-coax) into the surrounding outer dielectric wall 1409 and penetrate into the flesh/dielectric boundary where bacterial growth is present.

FIGS. 15A and 15B illustrate a schematic side cross-sectional view and a schematic end view, respectively, of another tube (e.g., a port, catheter, etc.) 1500 with dielectric walls inserted into flesh, according to an embodiment. In FIGS. 15A and 15B, conducting wires or strips 1510 are embedded into the dielectric walls of the tube 1500. In one embodiment, the inner surface 1508 and/or the outer surface 1509 of the tube 1500 is made electrically conducting, and electromagnetic energy (i.e., waves) is/are propagated within the dielectric portion of the tube walls 1508, 1509 and the region of flesh surrounding the port 1500 using the conducting wall and conducting wires/strips 1510 to guide the electromagnetic energy. In a different embodiment, the inner wall 1508 is non-conducting, and electromagnetic energy is guided down the structure using a combination of pairs of wires/strips 1510 such that electromagnetic energy is able to penetrate the dielectric/flesh boundary.

FIG. 16 illustrates a schematic side cross-sectional view of another tube (e.g., a port) 1600 with dielectric walls inserted into flesh, according to an embodiment. In FIG. 16, the dielectric material including the tube walls 1608, 1609 is such that it supports surface wave propagation with sufficient energy penetrating into the dielectric/flesh boundary to kill bacterial matter growing on this boundary. In one embodiment, the inner wall 1608 of the port 1600 is made conducting to aid in the support of this surface wave. In another embodiment, the inner wall 1608 is non-conducting and the dielectric properties of the port wall are sufficient to support surface wave propagation.

In summary, the system 100 and methods disclosed herein provide a microwave system for decontaminating medical tubing, ports and catheters, etc., operating within the human body. The contimanants include bacterial biofilms, fungi, parasites, viruses, and combination thereof. The system 100 and methods disclosed herein are designed to kill the contaminants while keeping temperature increases of the healthy body tissue below medically acceptable levels. The system 100 generates a signal having a frequency from about 10 GHz to 100 GHz. This signal can be adapted to kill one or more of the contaminants surrounding the medical tubing or inside the tubing. The output power and exposure time can be varied to accommodate various medical procedures and requirements (e.g., different catheter designs, functions and material markups). The system operations can varied by medical personnel to precisely control the temperature of the exposed tissue.

The system 100 is designed to utilize the natural body fluids to protect the healthy tissue. Tests have shown the penetration depth of the system's microwave energy is less than 1 mm thereby enabling most of the energy to be absorbed by the bacteria. The frequency selection and the antenna design are used to minimize the microwave penetration into the healthy tissue. The system 100 is designed for the microwave energy to interact directly with biofilms/bacteria. Test results have shown up to 99% bacteria kill rate in less than two minutes of time using less than 4 watts of microwave power.

An unexpected result is that the direct microwave heating threshold for ablating bacteria/biofilm is much lower than the temperature threshold for water bath bacterial kill. These unexpected results emphasize the importance of using selected very high frequency microwave energy for the ablation mechanism. Test results also indicate the dense inter-structure of biofilms absorb incident microwave energy. These unexpected results should aid in localizing the absorption of microwave energy to the nearby region outside of the catheter wall. The existence of fluid within the biofilm is also an advantage in localizing the tissue heating.

Patients may experience minimal or no discomfort during the medical treatment. The system 100 is versatile and can easily be adjusted to the patient's personal needs (e.g., exposure time, duration and power levels, as well as the type and use of the catheter). A doctor's presence may not be needed during treatment. A nurse can operate the equipment and treat the patient.

The antenna may be impedance matched to the catheter, the surrounding tissue, and/or the method of applying the energy during the treatment.

In one embodiment, the antenna exists separate from the catheter and is inserted through the opening at the catheter end. The antenna passes through the length of the catheter and delivers sufficient electromagnetic radiation to the areas of bacterial growth so as to kill the bacteria. In another embodiment, the antenna is integral with the catheter, and when energized, provides sufficient high-frequency electromagnetic radiation to kill bacterial growth that exists on the surfaces of the catheter. Segments of the antenna can be energized together or separately (in time) to expose more critical parts of the catheter for longer periods of time. The antenna can be made up of an array of separate (electrically) antenna components. It is possible to steer the beam electrically if a certain direction is desired. In yet another embodiment, the end-wall of a coax configuration may be adjustable using metamaterials with responses that vary according to frequency. With this arrangement, the peaks of the microwave signal can be moved up and down the length of the center coax to allow the microwave radiation to illuminate different portion of the catheter. In yet another embodiment, strategically placed temperature sensors on the outer wall of the catheter may be able to provide real-time adjustments to the radiating antenna to varying amounts of microwave energy to illuminate selected portions of the catheter. This feature can be useful in fine-tuning the microwave radiation pattern (profile).

The antenna delivery system can provide circularly symmetric radiation patterns, uniform illumination down the length of the catheter, and/or selective illuminating portions of the catheter. In another embodiment, the system 100 may be used to treat open wounds, infected areas, or abscesses. It is not necessary to use a port or catheter as the entry point into an infected area. Small antennas at the end of a coaxial cable or flexible waveguide can be inserted discreetly into an open wound. The microwave energy radiated directly into the infected area may be used in conjunction with standard antibiotics to kill the bacteria.

Figure 17:
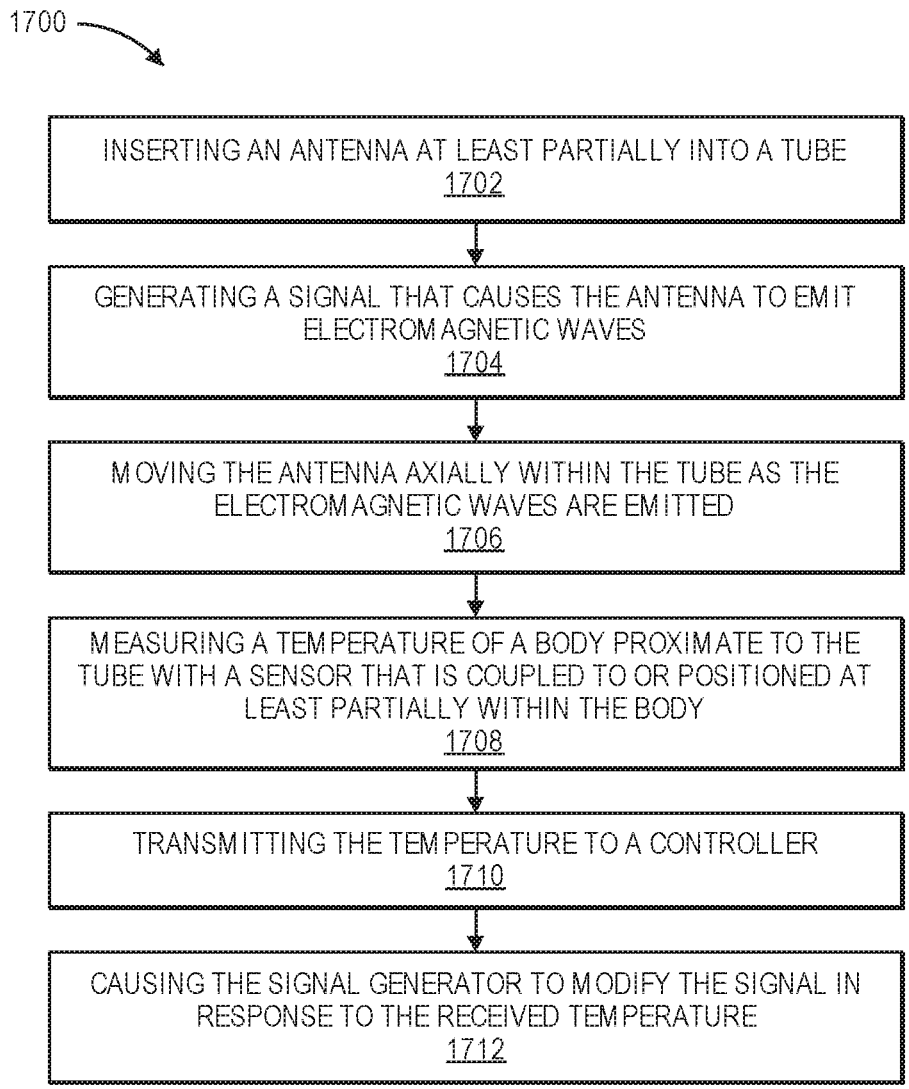
FIG. 17 illustrates a flowchart of a method for decontaminating a tube, according to an embodiment.

FIG. 17 illustrates a flowchart of a method 1700 for decontaminating a tube, according to an embodiment. The method 1700 may include inserting an antenna at least partially into a tube, as at 1702. The tube may be positioned at least partially within a body. The body may be part of a person or an animal. The body may include tissue, flesh, and/or fluids.

The method 1700 may also include generating a signal that causes the antenna to emit electromagnetic waves, as at 1704. The electromagnetic waves may at least partially decontaminate an interior and/or an exterior of the tube. The electromagnetic waves may have a frequency from about 10 GHz to about 100 GHz. The electromagnetic waves may cause a temperature of the body proximate to the tube to increase from about 0.1° C. to about 3° C. over a time duration from about 1 second to about 40 seconds. The method 1700 may also include moving the antenna axially within the tube as the electromagnetic waves are emitted, as at 1706.

The method 1700 may also include measuring the temperature of the body proximate to the tube (e.g., within 1 mm, 3 mm, or 5 mm of the tube) with a sensor that is coupled to or positioned at least partially within the body, as at 1708. The method 1700 may also include transmitting the temperature to a controller, as at 1710. The method 1700 may also include the controller causing the signal generator to modify the signal in response to the received temperature, as at 1712. Modifying the signal may include varying (e.g., reducing) the frequency of the signal, the duration of the signal, the power of the signal, or a combination thereof. This may reduce the temperature of the body proximate to the tube.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. Moreover, the order in which the elements of the methods are illustrated and described may be re-arranged, and/or two or more elements may occur simultaneously. The embodiments were chosen and described in order to best explain the principals of the invention and its practical applications, to thereby enable others skilled in the art to best utilize the invention and various embodiments with various modifications as are suited to the particular use contemplated.

What is claimed is:

1. A method for decontaminating a tube, comprising:
    positioning an antenna at least partially within a tube, wherein the tube is positioned at least partially within a living body; and
    decontaminating the tube by causing the antenna to emit electromagnetic waves having a frequency from about 10 GHz to about 100 GHz for a time duration that is less than or equal to 60 seconds, and wherein the electromagnetic waves cause a temperature of the living body proximate to the tube to increase from about 0.1° C. to about 3° C. so as to not substantially damage the living body.

2. The method of claim 1, further comprising moving the antenna axially within the tube as the electromagnetic waves are emitted.

3. The method of claim 1, further comprising:
    measuring the temperature of the living body proximate to the tube with a sensor; and
    transmitting the measured temperature to a controller.

4. The method of claim 3, further comprising modifying the frequency, the time duration, or a power of the electromagnetic waves using the controller when the temperature is greater than a predetermined threshold.

5. The method of claim 4, wherein modifying the frequency, the time duration, or the power of the electromagnetic waves causes the temperature of the living body proximate to the tube to decrease.

6. The method of claim 3, further comprising modifying the frequency, the time duration, or a power of the electromagnetic waves using the controller when the temperature increases by more than a predetermined threshold.

7. The method of claim 6, wherein modifying the frequency, the time duration, or the power of the electromagnetic waves causes the temperature of the living body proximate to the tube to decrease.

8. The method of claim 1, further comprising increasing the temperature of the living body proximate to the tube from about 0.1° C. to about 2° C. by varying a power of the electromagnetic waves between about 0.1 W and about 5 W.

9. The method of claim 1, wherein a power of the electromagnetic waves is less than or equal to 1 W, and wherein the electromagnetic waves cause the temperature of the living body proximate to the tube to increase by less than about 1° C. over the time duration.

10. The method of claim 1, wherein the living body comprises fluid and tissue, and wherein a penetration depth of the electromagnetic waves into the living body is less than about 1 mm when the frequency is from about 26.5 GHz to about 40 GHz.

11. A method for decontaminating a tube, comprising:
    positioning an antenna at least partially within a tube, wherein the tube is positioned at least partially within a living body;
    decontaminating the tube without substantially damaging the living body by causing the antenna to emit electromagnetic waves having a power from about 0.1 W to about 5 W and a frequency from about 10 GHz to about 100 GHz for a time duration that is less than or equal to 40 seconds, and wherein the electromagnetic waves cause a temperature of the living body proximate to the tube to increase by less than about 2.5° C.;
    measuring the temperature of the living body proximate to the tube with a sensor while the electromagnetic waves are emitted;
    transmitting the temperature of the living body proximate to the tube to a controller; and
    modifying the power, the frequency, the time duration, or a combination thereof of the electromagnetic waves with the controller when the temperature of the living body proximate to the tube is greater than a predetermined threshold, thereby causing the temperature of the living body proximate to the tube to decrease.

12. The method of claim 11, wherein the power is from about 0.1 W to about 2 W, wherein the frequency is from about 26.5 GHz to about 40 GHz, and wherein the electromagnetic waves cause the temperature of the living body proximate to the tube to increase by less than about 1° C.

13. The method of claim 11, wherein greater than about 75% of an energy from the electromagnetic waves is absorbed by the living body within 1 mm from the tube.

14. The method of claim 11, further comprising impedance-matching the antenna to the tube.

15. The method of claim 11, further comprising impedance-matching the antenna to the living body.

16. The method of claim 11, wherein the electromagnetic waves cause the temperature of the living body proximate to the tube to increase while remaining less than about 40° C. so as to not substantially damage the living body.

17. The method of claim 11, wherein the electromagnetic waves do not fuse or ablate the living body.

18. The method of claim 11, wherein positioning the antenna at least partially within the tube comprises positioning the antenna and a buffer at least partially within the tube, wherein the method further comprises moving the antenna and buffer axially within the tube, and wherein the buffer contacts an inner surface of the tube and prevents the antenna from contacting the inner surface of the tube.

19. The method of claim 11, wherein an inner portion of the tube comprises a radial aperture through which the electromagnetic waves travel, wherein the radial aperture does not extend through an outer portion of the tube, and wherein the outer portion of the tube comprises a dielectric material that is configured to receive the electromagnetic waves.

20. A method for decontaminating a tube, comprising:
- positioning an antenna and a buffer at least partially within a tube, wherein the tube is positioned at least partially within a living body;
- moving the antenna and the buffer axially within the tube, wherein the buffer contacts an inner surface of the tube and prevents the antenna from contacting the inner surface of the tube;
- decontaminating the tube without substantially damaging, fusing, or ablating any portion of the living body by causing the antenna to emit electromagnetic waves while the antenna moves axially within the tube, wherein the electromagnetic waves have a power from about 0.1 W to about 5 W and a frequency from about 10 GHz to about 100 GHz, wherein the electromagnetic waves are emitted for a time duration that is less than or equal to 40 seconds, wherein greater than about 75% of an energy from the electromagnetic waves is absorbed by the living body within 1 mm from the tube, and wherein the electromagnetic waves cause a temperature of the living body proximate to the tube to increase by less than about 2.5° C. while the temperature of the living body does not exceed 40° C.;
- measuring the temperature of the living body proximate to the tube with a sensor that is coupled to an outer surface of the tube;
- transmitting the measured temperature of the living body proximate to the tube to a controller; and
- modifying the power, the frequency, the time duration, or a combination thereof of the electromagnetic waves with the controller when the temperature of the living body proximate to the tube is greater than a predetermined threshold, thereby causing the temperature of the living body proximate to the tube to decrease.

* * * * *